US011871793B1

(12) United States Patent
Abehasera

(10) Patent No.: US 11,871,793 B1
(45) Date of Patent: Jan. 16, 2024

(54) SMART ELECTRONIC SMOKING DEVICE

(71) Applicant: Benyamin Abehasera, Boca Raton, FL (US)

(72) Inventor: Benyamin Abehasera, Boca Raton, FL (US)

( * ) Notice: Subject to any disclaimer, the term of this patent is extended or adjusted under 35 U.S.C. 154(b) by 0 days.

(21) Appl. No.: 18/347,675

(22) Filed: Jul. 6, 2023

(51) Int. Cl.
| | |
|---|---|
| *A24F 40/485* | (2020.01) |
| *A24F 40/10* | (2020.01) |
| *A24F 7/00* | (2006.01) |
| *A24F 40/90* | (2020.01) |
| *A24F 40/60* | (2020.01) |
| *A24F 40/85* | (2020.01) |
| *A24F 40/30* | (2020.01) |
| *A24F 40/51* | (2020.01) |
| *A24F 40/57* | (2020.01) |
| *A24F 40/65* | (2020.01) |
| *A61L 9/20* | (2006.01) |
| *A24F 40/42* | (2020.01) |

(52) U.S. Cl.
CPC ............. *A24F 40/485* (2020.01); *A24F 7/00* (2013.01); *A24F 40/10* (2020.01); *A24F 40/30* (2020.01); *A24F 40/42* (2020.01); *A24F 40/51* (2020.01); *A24F 40/57* (2020.01); *A24F 40/60* (2020.01); *A24F 40/65* (2020.01); *A24F 40/85* (2020.01); *A24F 40/90* (2020.01); *A61L 9/20* (2013.01); *A61L 2209/12* (2013.01)

(58) Field of Classification Search
CPC .......... A24F 40/30; A24F 40/10; A24F 40/40; A24F 40/485
See application file for complete search history.

(56) References Cited

U.S. PATENT DOCUMENTS

| | | | |
|---|---|---|---|
| 9,888,725 B2 | 2/2018 | Cameron et al. | |
| 10,212,971 B2* | 2/2019 | Cameron | ................ A24F 40/05 |
| 10,343,818 B2* | 7/2019 | Murphy | ................ B65D 43/16 |
| 10,506,830 B2* | 12/2019 | Li | .......................... A61M 15/06 |
| 11,504,486 B2* | 11/2022 | Gallagher | ............... A24F 40/30 |
| 2019/0158938 A1* | 5/2019 | Bowen | .............. H04M 1/72415 |
| 2021/0045457 A1* | 2/2021 | Weigensberg | .......... A24F 40/42 |

* cited by examiner

*Primary Examiner* — Hae Moon Hyeon
(74) *Attorney, Agent, or Firm* — Geoffrey Lottenberg; Berger Singerman LLP

(57) ABSTRACT

A smart electronic smoking device that includes a main body having a mouthpiece disposed at one end and an internal space. The mouthpiece of the smoking device includes an open terminal end with a flow dispersing member designed to provide at least two inhalation outlets to allow inhaled smoke from the smoking device to disperse evenly within the user's oral cavity. The smoking device also includes an inhalation material container and a plurality of electronic components that monitor and display inventory levels of the inhalation material, such as vaping liquid, available to the user, and user usage rate of the smoking device. The inhalation material container includes an upper chamber and a lower chamber that are connected by a conduit that allows the passage of inhalation material from the lower chamber to the upper chamber.

20 Claims, 8 Drawing Sheets

SMART ELECTRONIC SMOKING DEVICE

FIELD OF THE INVENTION

The present invention relates generally to electronic smoking devices, and more particularly, to a smart electronic smoking device that includes one or more electronic components configured to moderate and track the user's usage of the smoking device.

BACKGROUND OF THE INVENTION

Electronic smoking devices in general have not significantly changed since entering the market in the mid-2000s. Although certain features of electronic smoking devices or e-cigarettes as otherwise known over the past few years have been refined to eliminate catastrophic failures that lead to personal injuries (e.g., vape fires or explosions due to gas or liquid leaks), the basic features of an electronic smoking device remain the same. One such feature is the mouthpiece structure of the smoking device. Traditional mouthpieces are designed for comfort but are severely deficient. For instance, one particular drawback with traditional mouthpieces is that they cause stomatitis—painful swelling of the upper palate of the user's mouth—because the mouthpiece is designed to allow a concentrated amount of smoke directly to a singular point on the upper palate of the user when inhaling, thereby causing damage to the mouth of the user.

Additional issues with traditional smoking devices is that they are difficult to charge because they include an integrated charging port that may not be compatible with surrounding charging stations, they do not monitor the consumption rate of the user to moderate usage of the device that can lead to a health crisis, track liquid cartridge levels to notify the user that a replacement cartridge will soon be necessary, or provide alternative liquid and nicotine mixture options at the preference of the user other than the available pre-manufactured liquid cartridges sold with the device or sold as available replacement cartridges. Further drawbacks with traditional smoking devices include smoking devices that are incapable of adapting or otherwise adjusting the temperature of the vape or the amount of vape that is drawn from the smoking device by the user based on the lung capacity (i.e., inhalation-pressure) of the user.

Accordingly, there is an established need for a smart electronic smoking device that improves upon at least one of the aforementioned shortcomings.

SUMMARY OF THE INVENTION

The present invention is directed to a smart electronic smoking device that includes a main body having a mouthpiece disposed at one end and an internal space. The mouthpiece of the smoking device includes an open terminal end with a flow dispersing member designed to provide at least two inhalation outlets to allow inhaled smoke from the smoking device to disperse evenly within the user's oral cavity. The smoking device also includes an inhalation material container and a plurality of electronic components that monitor and display inventory levels of the inhalation material, such as vaping liquid, available to the user, and user usage rate of the smoking device.

Introducing a first embodiment of the invention, the present invention consists of a smart electronic smoking device a main body having a proximal end and a distal end, and including an internal space;

a mouthpiece provided at the proximal end of the main body, the mouthpiece including an open terminal end having a flow dispersing member disposed thereon;

one or more electronic components disposed within the internal space;

a compartment space for storing a charging member in communication with at least one electronic component; and at least one electronic indicator disposed on the main body and in communication with at least one electronic component.

In another aspect, the flow dispersing member projects may include an arched body that projects beyond the open terminal distal end of the mouthpiece and is configured to provide at least two inhalation outlets.

In another aspect, the electronic indicator may comprise one or more LEDs or a digital display. The LEDs and the digital display are in electronic communication with the microcontroller, whereupon the microcontroller is designed or otherwise configured to control both electronic indicators.

In another aspect, the electronic components may comprise a heating element, a sensor a microcontroller, a wireless adapter and a power source configured to power the electronic components. The wireless adapter module is in communication with the microcontroller and configured to allow communication between the microcontroller and an electronic device, such as a smart phone, configured to run an application.

In another aspect, the internal space of the main body is configured to retain an inhalation material container that may retain ambient air or a liquid mixture. Alternatively, the internal space of the main body may be configured to retain at least two inhalation material containers retaining inhalation material that are in fluid communication. The electronic smoking device may further include a valve mechanism in communication with one inhalation material container, the valve mechanism configured to control inhalation material flow from the one inhalation material container to the other.

In another aspect, the smart electronic smoking device may include an LED disposed within the internal space of the main body, the LED configured to emit light of a wavelength effective for neutralizing bacteria and viruses. The LED light, in one exemplary form, cleanses the vape and the heating element of the smoking device during use.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As used herein, the terms "puff," "drag," or "inhale," means to draw on the smart electronic smoking device with intermittent exhalations of smoke or to breathe smoke from the smart electronic smoking device.

As used in this specification and the appended claims, the singular forms "a," "an," and "the" include plural referents unless the content clearly dictates otherwise, and vice versa. It should also be noted that the term "or" is generally employed in its broadest sense, that is as meaning "and/or" unless the content clearly dictates otherwise.

Figure 1:
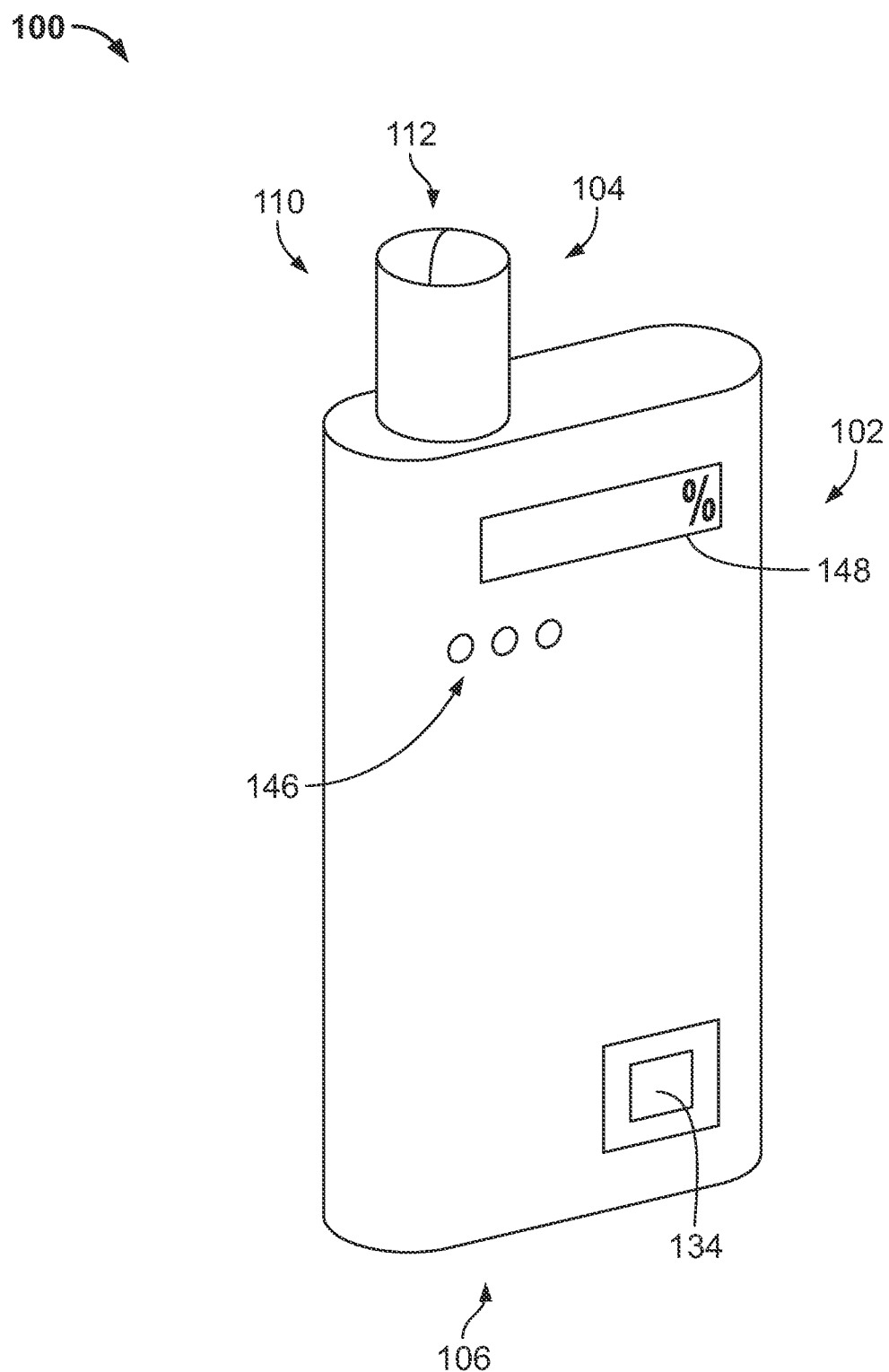
FIG. 1 presents a front perspective view of the smart electronic smoking device.
Figure 2:
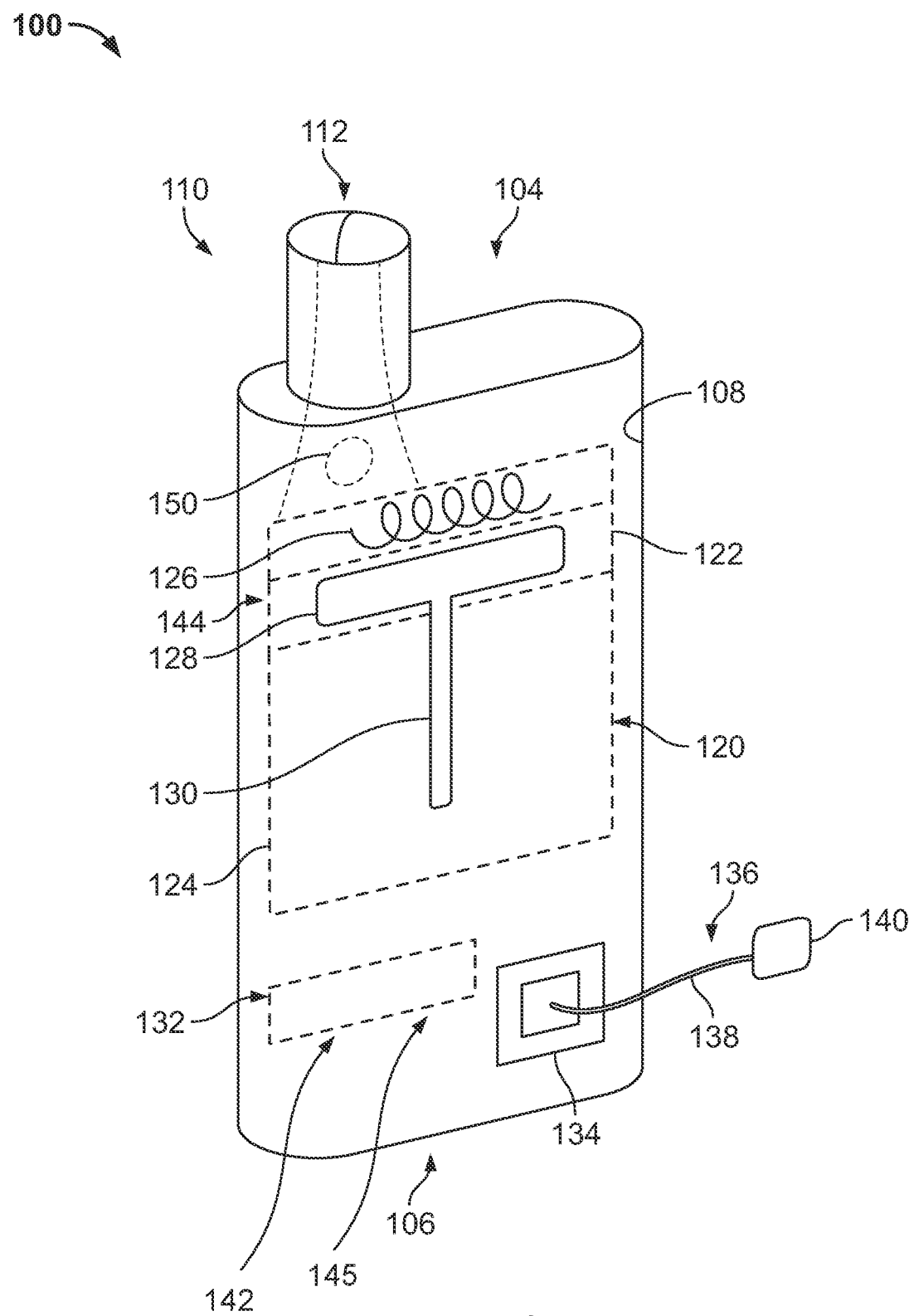
FIG. 2 presents a front perspective view of the smart electronic smoking device showing various components disposed therein.
Figure 4:
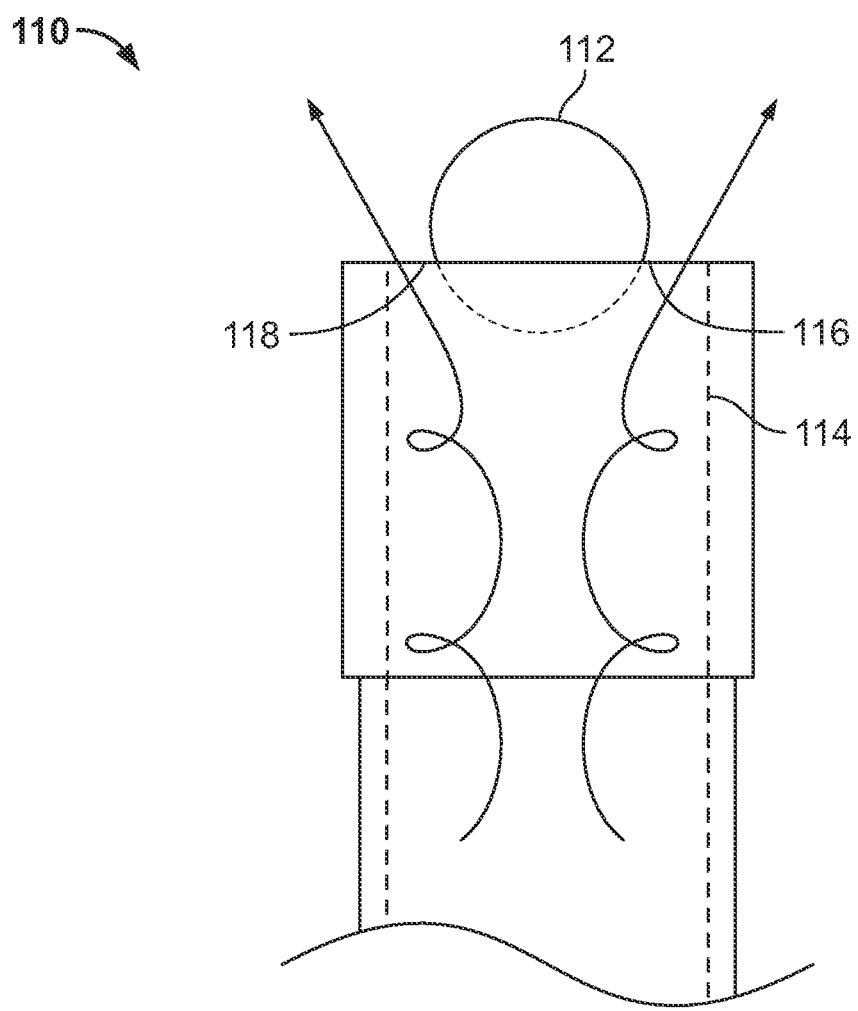
FIG. 4 presents an enlarged front elevation view of the mouthpiece of the smart electronic device.

Referring initially to FIGS. 1-2, and 4, a smart electronic smoking device 100 (hereinafter "smoking device") is generally shown. The smoking device 100 in one exemplary embodiment comprises a main body 102 having a proximal end 104 and an opposing distal end 106. At the proximal end 104 of the main body 102 is a mouthpiece 110 that includes a terminal open end, a mouthpiece passageway 114 (see FIG. 4) that allows smoke to pass therethrough, and a flow dispersing member 112 that generally provides a first inhalation outlet 116, and a second inhalation outlet 118. The flow dispersing member 112 is design and otherwise configured to allow inhaled smoke from the smoking device to disperse evenly within the user's oral cavity, rather than allowing a concentrated amount of hot smoke to be directed at a singular point on the upper palate of the user. In one exemplary embodiment, the flow dispersing member 112 disposed on the terminal open end of the mouthpiece 110 includes an arched body that projects beyond the terminal open end and may include beveled or rounded surfaces to create the desired airflow effect, as exemplary shown in FIG. 4.

Returning to FIGS. 1-2, the smoking device 100 also includes an inhalation material container 120 disposed inside of the internal space 108 of the main body 102. The inhalation material container 120, in one exemplary embodiment, comprises an upper chamber 122 and a lower chamber 124 that are in fluid communication via a conduit 130. The conduit 130 in one exemplary form may comprise a capillary tube. The lower chamber 124 of the inhalation material container 120 is filled with inhalation material, such as vape liquid or in some instances ambient air. The upper chamber 122 of the inhalation material container 120 includes ignitable material 128, such as cotton strips, and a heating element 126, such as a heating coil. Inhalation material stored within the lower chamber 124 of the inhalation material container 120 is drawn through the conduit 130 and changed into vapor that is dragged from the mouthpiece 110 of the smoking device 100. As the user is inhaling inhalation material, the smoking device 100 of the instant invention in one exemplary embodiment may include a sanitation element 150, such as a light-emitting diode (LED) capable of emitting light at a cleansing wavelength in the range of 100-280 nm, and more particularly, in the range of 200-280 nm to effectively neutralize microorganisms such as bacteria, viruses, and the like that may be floating in the inhalation material being inhaled by the user and bacteria growing in any one of the internal components (e.g., the heating element).

The smoking device 100 also includes a number of electronic components 132, such as sensors 144 capable of gathering data, a power source 145, a microcontroller 142, light-emitting diodes (LEDs) 146, and a digital display 148, all of which are powered by the power source. The term processor, as used herein, refers to central processing units, microprocessors, microcontrollers, reduced instruction set circuits (RISC), application specific integrated circuits (ASIC), logic circuits, and any other circuit or processor capable of executing the functions described herein. As used herein, the terms "software' and "firmware" are interchangeable, and include any computer program stored in memory for execution by the processor, including random-access memory (RAM), read-only memory (ROM), erasable programmable read-only (EPROM), electrical erasable programmable read-only (EPROM), and non-volatile RAM (NVRAM) memory. The above memory types are exemplary only, and are thus not limiting as to the types of memory usable for storage of a computer program.

In one exemplary embodiment, the power source may comprise a rechargeable Lithium Ceramic Battery. The power source is connected to a charging member 136 that includes a charging cable 138 and a charging head 140. The charging head 140 of the charging member 136 may comprise a universal serial bus (USB), such as USB-A, USB-B, USB-C, USB Micro-A, USB Micro-B, USB Mini-A, or USB Mini-B. Alternative charging heads not readily described herein may be utilized, therefore, the foregoing list of charging heads should be understood to be exemplary and not limiting. In one exemplary embodiment, the charging member 136 may comprise an integrated foldable on-the-go (OTG) USB Type-C cable or a sliding USB-C, male type that includes an OTG, which would allow the smoking device to be charged directly from an electronic device, such as a mobile phone. In this exemplary configuration, the power source of the smoking device 100 could be charged directly through a smartphone, tablet, computer, or portable device without any external charging adapter or charging traditional 5V dc charging block. As seen in FIG. 2, the charging member 136 of the smoking device 100 is stored within a storage compartment 134 of the main body 102 of the device with the compartment 134 being sufficiently sized to retain all of the charging member 136 therein. Put differently, when the charging member 136 is stored in the storage compartment 134, the charging member 136 is not visible to the user and does not impede the user from comfortably grasping the main body 102 of the smoking device 100.

Figure 5:
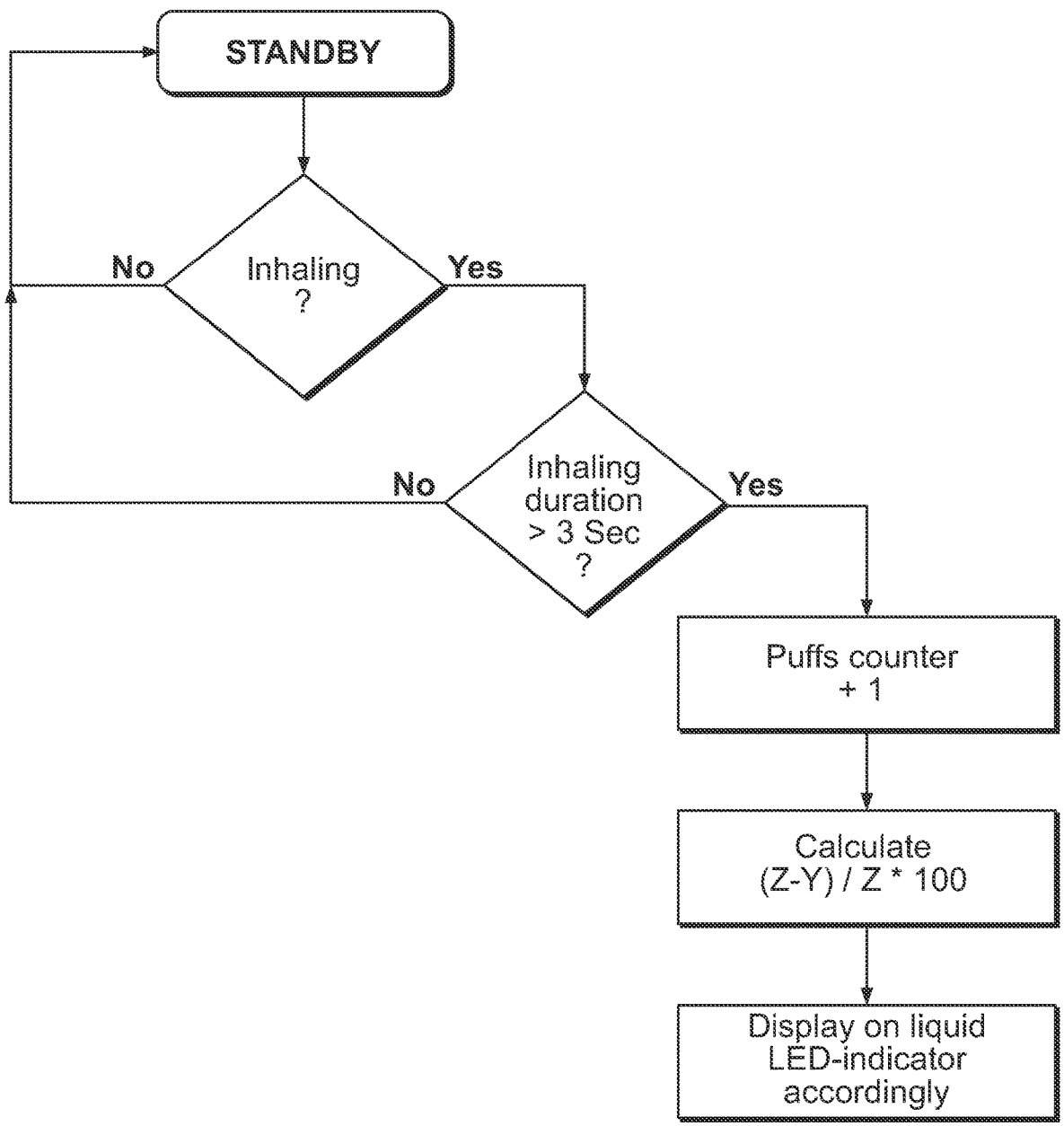
FIG. 5 presents a block diagram showing the smart electronic smoking device tracking the consumption rate of the user displaying at least the amount of liquid available in the liquid cartridge.

With quick reference now to FIG. 1, as iterated above, the smoking device 100 includes one or more light emitting diodes (LEDs) 146 disposed about the main body 102 of the device, and a digital display 148. Both the digital display 148 and the LEDs 146 are in electronic communication with the microcontroller 142. Accordingly, the microcontroller 142 is programmed with logic stored in an internal memory bank to execute one or more commands that otherwise control one or more functions of the electronic smoking device 100. For instance, the microcontroller 142 is in electronic communication with a sensor that is configured to capture data on the available levels of inhalation material inside of the inhalation material container 120. The microcontroller 142 upon receiving the data automatically begins to execute programmed commands. An exemplary flow of the programmable commands or steps performed by the microcontroller 142 can be found in FIG. 5. As exemplary illustrated, during non-use of the smoking device 100, the microcontroller 142 is otherwise in standby mode awaiting a response to a query, that exemplary being whether the user is utilizing the device to inhale inhalation material. If the answer is no, the microcontroller remains in standby. If the answer is yes, meaning the sensor detects that the user is inhaling, the microcontroller activates a puff counter. If the inhalation period is greater than a time variable, for example 3 seconds, the puff is added to the puff counter and the count of puffs continues to grow sequentially every time the user utilizes the smoking device 100. If on the other hand the inhalation period is less than the established time variable, the puff is not counted. The puff count Y is then compared to the total amount of available puffs Z the inhalation material container 120 provides to calculate the remaining percentage of inhalation material available inside of the inhalation material container 120. Once the value is determined by the microcontroller 142, a signal from the controller is sent to the digital display and a displayable value, such as percentage amount, is digitally displayed for the user to see. In one exemplary form, the value may comprise a percentage amount of available inhalation material (e.g., 51%). Alternatively, the value may be a numerical comparison of available inhalation material (e.g., 40 of 60 puffs remain). Of course, the displayable value utilized to show the amount of inhalation material available can vary from the above described, therefore, the foregoing should be understood to be exemplary and not limiting.

Figure 6:
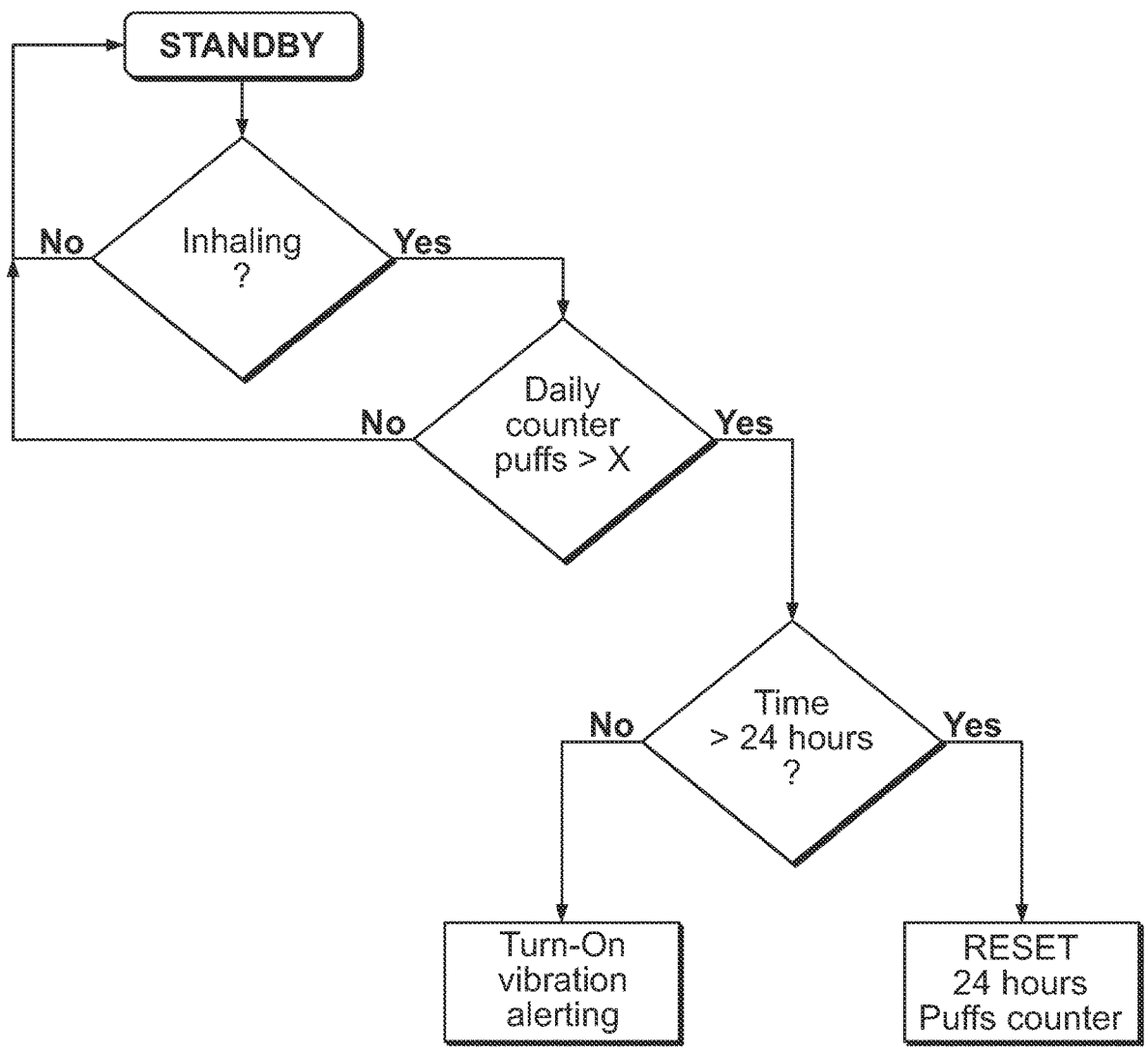
FIG. 6 presents a block diagram showing the smart electronic smoking device tracking the number of drags taken by the user within a defined time period.
Figure 7:
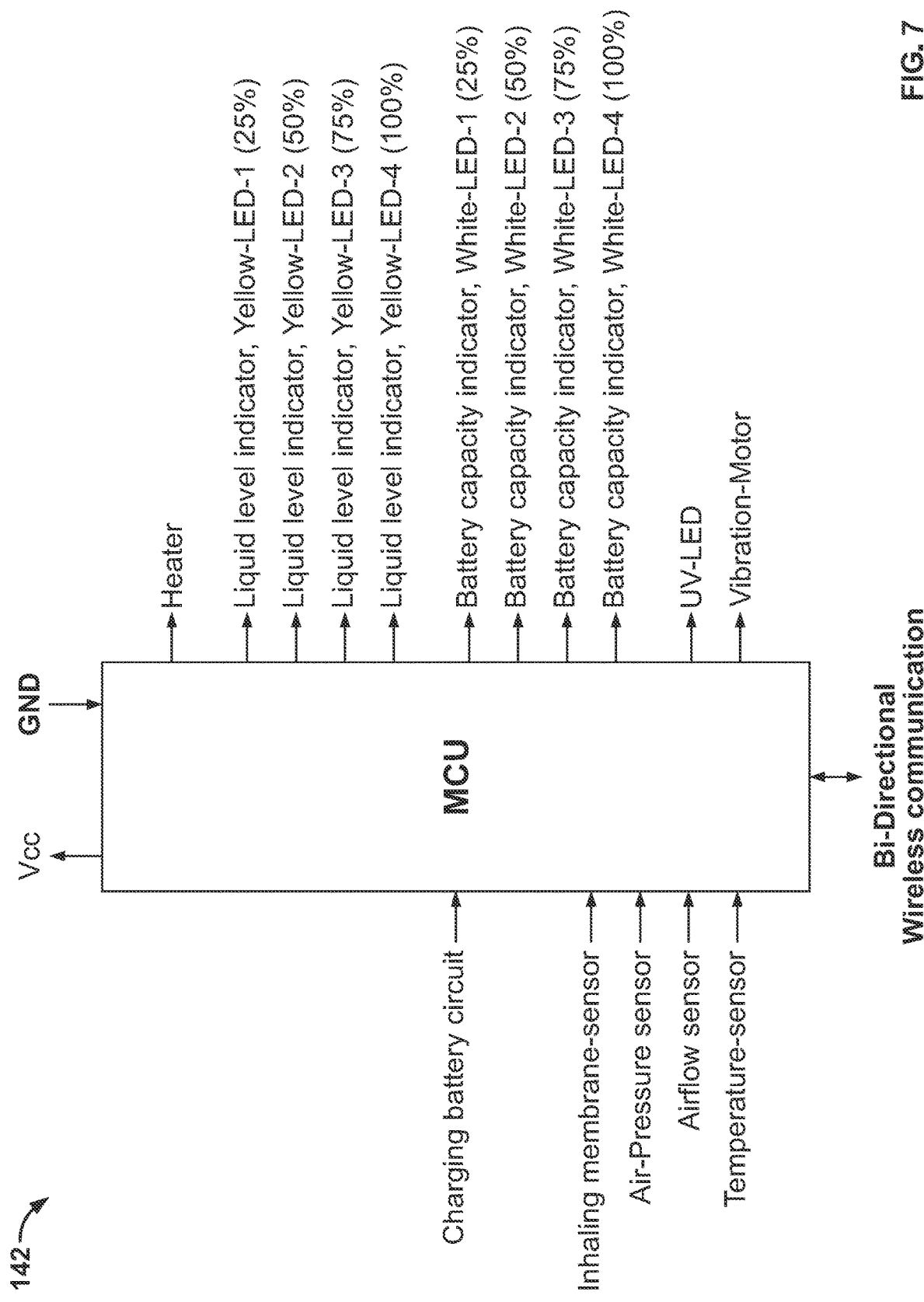
FIG. 7 presents a schematic of the microprocessor and various electronic components of the smart electronic smoking device.

With reference to FIGS. 1, 6, and 7, the microcontroller 142 is also in electronic communication with a sensor that is configured to gather data on the user's usage rate of the smoking device 100. For instance, the microcontroller 142 includes an internal timer module that works in tandem with one or more additional components, including a sensor, to track the number of puffs "X" or drags taken by the user in a single day. As utilized herein, the term "single day" is understood to be a 24-hour period starting at 12:00 AM and ending at 11:59 PM daily. As described above, during non-use of the smoking device 100, the microcontroller 142 is in standby mode awaiting a response to a query, that being whether the user is utilizing the device to inhale inhalation material. If the answer is no, the microcontroller remains in standby. If the answer is yes, meaning the sensor detects that the user is inhaling, the microcontroller begins the puff counter. The puff counter continues to tally the puff count throughout the day. Programmed to the microcontroller is at least one threshold value representing a threshold number of puffs by the user within a 24-hour period that if exceeded, the microcontroller 142 sends a signal to the electronic indicator, such as LEDs 146, to emit a light warning or turn on a vibration alert. After the 24-hour period lapses (e.g., 11:59 PM), the puff counter resets back to zero.

In one exemplary form, the microcontroller may be programmed to include a first threshold value of 500 puffs, a second threshold value of 750 puffs, and a third threshold value of a maximum of 1,000 puffs. As described above, the microcontroller 142 tracks the number of puffs by the user. If the user exceeds the first threshold value, the microcontroller 142 sends a signal to the electronic indicator to turn on an LED and displays a color (e.g., green), informing the user know that the first threshold of 500 puffs has been reached. If the user exceeds the second value threshold, a second LED light turns on and displays a color (e.g., yellow), informing the user know that the second threshold of puffs has been reached. Similarly, if the user exceeds the third value threshold, a third LED light turns on and displays a color (e.g., red), informing the user know that the maximum threshold of puffs has been reached. Of course, the number of LEDs used may be varied from foregoing or an alternative signaling system be used (e.g., a display device), and therefore, the aforementioned should be considered exemplary and not limiting. For example, in lieu of the LEDs signaling the user has exceeded the puff value thresholds, the smoking device 100 may include a vibration motor that causes the device to vibrate and warn the user or a shut-off system that prevents the user from inhaling smoke beyond the maximum threshold count.

As seen in FIG. 7, the microcontroller 142 may also include a wireless communication module that is configured to communicate with an electronic device operating an application over a network. A network may include wireless communication including but not limited to: WLAN (wireless local area network, Wi-Fi, (IEEE 802.011), WPANS (wireless personal area networks, such as Bluetooth (IEEE 802.15), Infrared, ZigBee, WMAN (wireless metropolitan area network, such as WiMax (IEEE 802.16)), WWAN (wireless wide area networks, internet), and GAN (global area network), An electronic device, as used herein, refers to a device with a processor, memory, network interface, and a storage device. Electronic devices are capable of executing instructions. The term electronic device includes, but is not limited to, a personal computer, server computers, computing tablets, set-top boxes, video game systems, personal video recorders, telephones, cellular telephones, digital telephones, personal digital assistants (PDAs), portable computers, notebook computers, and laptop computers. Electronic devices may run an operating system (OS), including, for example, variations of the Linux, Unix, MS-DOS, Microsoft Windows, Palm OS, Symbian OS, and Apple Mac OS X operating systems. Electronic devices also include communications software that allows for communication over network. Depending on the electronic device, the communications software may provide support for communications using one or more of the following communications protocols or standards: the User Datagram Protocol (UDP), the Transmission Control Protocol (TCP), the Internet Protocol (IP), and the Hypertext Transport Protocol (HTTP); one or more lower-level communications standards or protocols such as, for example, the 10 and/or 40 Gigabit Ethernet standards, the Fiber Channel standards, one or more varieties of the IEEE 802 Ethernet standards, Asynchronous Transfer Mode (ATM), X.25. Integrated Services Digital Network (ISDN), token ring, frame relay, Point to Point Protocol (PPP), Fiber Distributed Data Interface (FDDI); and other protocols. Electronic devices may include a network interface card, network chip, or network chipset that allows for communication over network.

Figure 8:
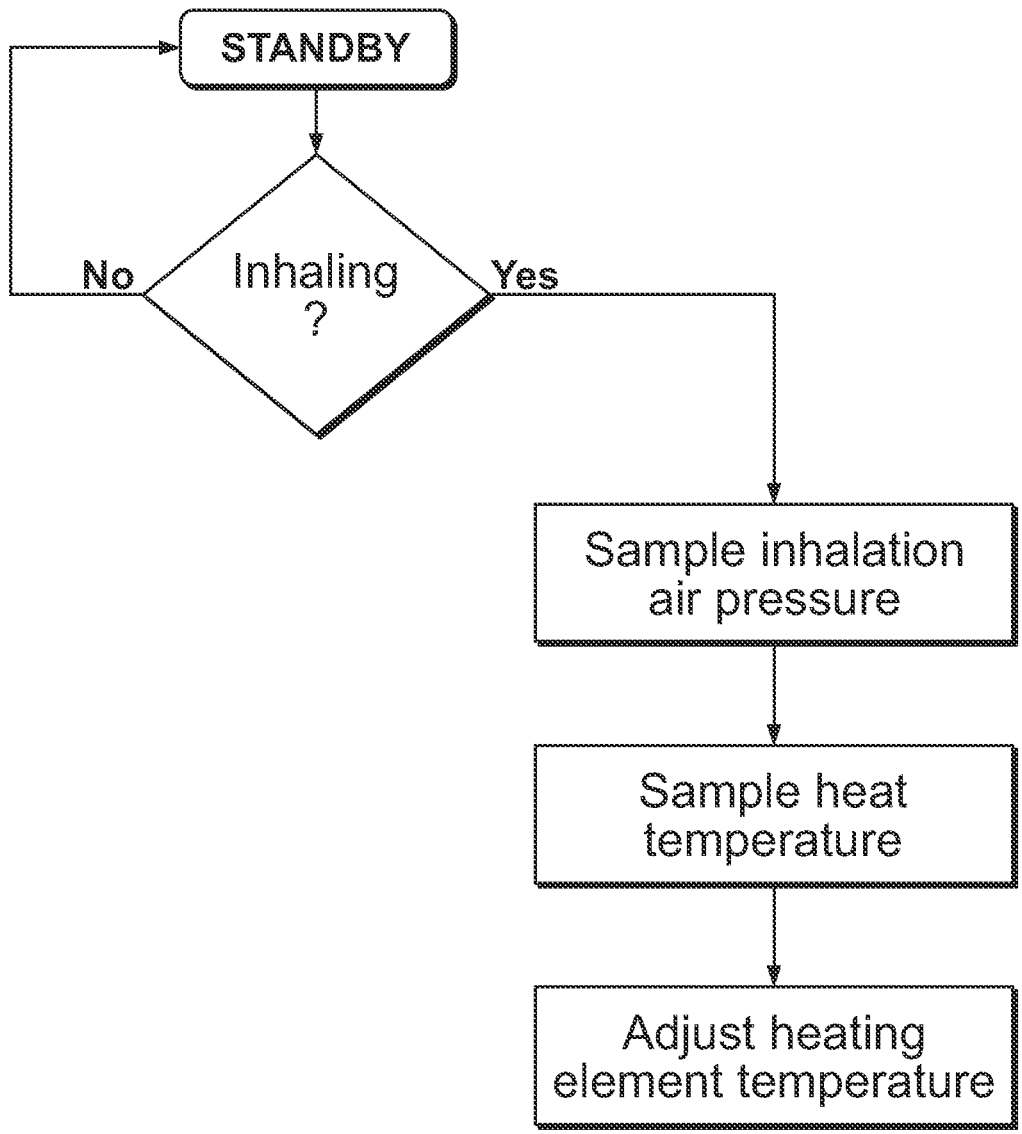
FIG. 8 presents a block diagram showing the smart electronic smoking device sampling air-pressure and heat temperature of inhalation material and adjusting the temperature of the heating element to adjust the temperature of inhalation material during inhalation.

The microcontroller 142 of the smoking device 100, in one exemplary embodiment, is connected to a pressure and temperature sensor that are configured to capture data relating to the air-pressure and the temperature of the inhalation material being dragged from the smoking device 100 by the user. The microcontroller 142 upon receiving the data automatically begins to execute programmed commands to adjust the heating element 226a,b of the smoking device 100 to adjust the temperature of the inhalation material being ingested. An exemplary flow of the programmable commands or steps performed by the microcontroller 142 can be found in FIG. 8. As exemplary illustrated, during non-use of the smoking device 100, the microcontroller 142 remains in standby mode awaiting a response to the query whether the device is being utilized to inhale inhalation material. While there is non-use of the device, the smoking device remains in standby. On the other hand, if the smoking device detects the user is inhaling through one of its multiple sensors, the air-pressure sensor and heat temperature sensor of the present device begin to collect data and transmit that data to the microcontroller 142. The microcontroller 142 analyzes the inhalation pressure, which is directly correlated to the lung capacity of the user. The microcontroller 142 also analyzes the temperature of the inhalation material captured by the sensor. Dependent on the variable of the inhalation pressure and the temperature reading captured by the sensors, the microcontroller sends a signal to the heating element 126 to modulate its heating temperature. In turn, the inhalation material inhaled by the user is cooled or heated to a more pleasurable level. For instance, if the inhalation material temperature is too high (i.e., too hot) because of the inhalation pressure provided by the user, the microcontroller sends a signal to the heating element to lower its heating temperature to effectively lower the temperature the inhalation material is ingested.

Figure 3:
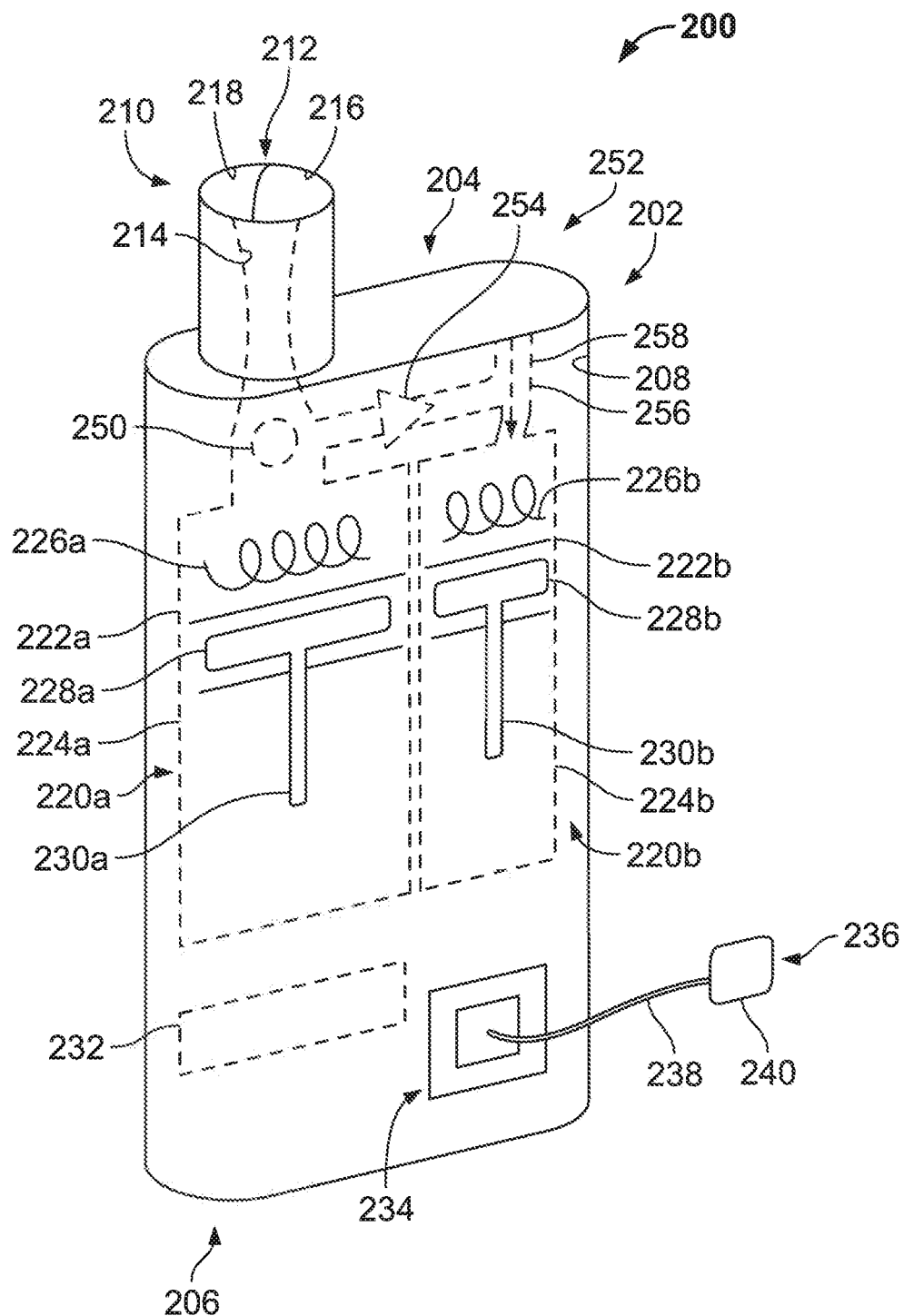
FIG. 3 presents a front perspective view of an alternative embodiment of the smart electronic smoking device showing various components disposed therein.

With reference now to FIG. 3, a second embodiment of the smoking device 200 is generally shown. The smoking device 200 is similar to the smoking device 100 described herein above. Accordingly, similar features of the smoking device 200 are number identically to the similar features of the smoking device 100, with the exception that the smoking device features are prefixed with the '2.' The smoking device 200 generally comprises a main body 202 having a proximal end 204 and an opposing distal end 206. At the proximal end 204 of the main body 102 is a mouthpiece 210 that includes a terminal open end, a mouthpiece passageway 214 that allows smoke to pass therethrough, and a flow dispersing member 212 that generally provides a first inhalation outlet 216, and a second inhalation outlet 218. The smoking device 200 also includes a number of electronic components 232, such as sensors capable of gathering data, a power source, a microcontroller 142, light-emitting diodes (LEDs), and a digital display, all of which are powered by the power source. The smoking device 200 includes a charging member 236 that includes a charging cable 238 and a charging head 240. The charging member 236 of the smoking device 200 is stored within a storage compartment 234 of the main body 202 of the device with the compartment 234 being sufficiently sized to retain the charging member 236 therein.

With continued reference to FIG. 3, in this exemplary embodiment the smoking device 200 includes at least two inhalation material containers 220a,b disposed inside of the internal space 208 of the main body 202. Both inhalation material containers 220a,b comprise an upper chamber 222a,b, and a lower camber 224a,b that are in fluid communication via conduit 230a,b. The conduit may comprise a capillary tube or the like. The lower chamber 224a,b of the inhalation material containers 220a,b may be filled with different inhalation materials. For instance, the first inhalation material container 220a may be filled with inhalation material that is devoid of nicotine, whereas the second inhalation material container 220b may be filled with inhalation material that contains nicotine. The upper chamber 222a,b of the inhalation material containers 220a,b includes ignitable material 228a,b, such as cotton strips, and a heating element 226a,b, such as a heating coil. Inhalation material stored within both lower chambers 224a,b of the inhalation material container 220a,b is drawn through the conduit 230a,b and changed into vapor that is dragged from the mouthpiece 210 of the smoking device 200. As the user is inhaling inhalation material, the smoking device 200 of the instant invention in one exemplary embodiment may include a sanitation element 250, such as a light-emitting diode (LED) capable of emitting light at a cleansing wavelength in the range of 100-280 nm, and more particularly, in the range of 200-280 nm to effectively neutralize microorganisms such as bacteria, viruses, and the like that may be floating in the inhalation material being inhaled by the user. The sanitation element sanitizes in addition to the inhalation material, the components located within the main body 202 of the smoking device. Those components include, but are not limited to the heater 226a,b of the heating element during use and non-use of the smoking device.

As an added feature, the smoking device 200 includes a valve mechanism 252 designed to control the flow of inhalation material from one inhalation material container 220b to the other inhalation material container 220a. The valve mechanism 252 comprises a valve knob 254 disposed on the main body 202 of the smoking device 200 that controls a valve head 256 disposed in a conduit 258 that connects both inhalation material containers 220a,b, and is configured to enable or disable flow of inhalation material from the inhalation material container 220b to mix with the inhalation material container 220a of the smoking device 200. In this exemplary configuration, a user may opt to have one inhalation material container to include inhalation material devoid of nicotine and another with nicotine and decide when to inhale a mixture of nicotine infused inhalation material by manipulating the control valve mechanism 252 of the smoking device 200. In one exemplary embodiment, the inhalation material devoid of nicotine can be infused with nicotine from the inhalation material container comprising nicotine in a controlled percentage amount via the control valve mechanism 252. The percentage amount, in one exemplary form, comprises an adjustable amount of 0% to X % of nicotine. The amount of nicotine mixed with the inhalation material devoid of nicotine is displayable on the digital display of the smoking device. In some instances, the upper bound of nicotine mixed with the inhalation material may be as high as 25% or higher.

As described above, the smoking device 200 includes a microcontroller 142 that is programmed with logic stored in an internal memory bank to execute one or more commands that otherwise control one or more functions of the electronic smoking device 200. Accordingly, the smoking device 200 is capable of displaying the available levels of inhalation material inside of each the inhalation material container 220a,b, and track the number of puffs the user has on a daily basis.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. An electronic smoking device, comprising:
a main body having a proximal end and a distal end, and including an internal space;
a mouthpiece provided at the proximal end of the main body, the mouthpiece including an open terminal end having a flow dispersing member disposed thereon, the flow dispersing member projecting beyond an inhalation outlet at the open terminal end of the mouthpiece;
one or more electronic components disposed within the internal space;
a compartment space provided in the main body for storing a charging member in communication with at least one electronic component; and
at least one electronic indicator disposed on the main body and in communication with at least one of the one or more electronic components.

2. The electronic smoking device of claim 1, wherein the flow dispersing member is configured to provide at least two inhalation outlets.

3. The electronic smoking device of claim 1, wherein the at least one electronic indicator comprises one or more light emitting diodes (LEDs).

4. The electronic smoking device of claim 1, wherein the electronic indicator comprises a digital display.

5. The electronic smoking device of claim 1, wherein an LED is disposed within the internal space of the main body, the LED configured to emit light of a wavelength effective for neutralizing bacteria and virus growth within the internal space of the main body.

6. The electronic smoking device of claim 1, wherein the internal space of the main body is configured to retain at least two inhalation material containers retaining inhalation material and are in fluid communication.

7. The electronic smoking device of claim 6, wherein the electronic smoking device includes a valve mechanism in communication with one inhalation material container, the valve mechanism configured to control inhalation material flow from the one inhalation material container.

8. The electronic smoking device of claim 1, wherein the internal space of the main body is configured to retain an inhalation material container that retains ambient air.

9. The electronic smoking device of claim 1, wherein the one or more electronic components include a heating element, at least one sensor, a microcontroller, and a power source configured to power the electronic components.

10. The electronic smoking device of claim 9, wherein the microcontroller is in electronic communication with the at least one sensor and capable of regulating the heating element's heat output based on data from the at least one sensor.

11. The electronic smoking device of claim 10, wherein the microcontroller is in electronic communication with and controls the at least one electronic indicator.

12. The electronic smoking device of claim 1, wherein the one or more electronic components comprise a wireless adapter module in communication with a microcontroller, the wireless adapter module configured to allow communication between the microcontroller and an electronic device configured to run an application.

13. The electronic smoking device of claim 1, further comprising at least one inhalation material container disposed within the internal space that includes an upper chamber, a lower chamber, and a conduit configured to pass inhalation material from the lower chamber toward the upper chamber.

14. An electronic smoking device, comprising:
a main body having a proximal end and a distal end, and including an internal space;
a mouthpiece provided at the proximal end of the main body, the mouthpiece including an open terminal end having a flow dispersing member disposed thereon, the flow dispersing member projecting beyond an inhalation outlet at the open terminal end of the mouthpiece;
at least one inhalation material container disposed within the internal space configured to retain an inhalation material;
a plurality of electronic components that include a heating element, at least one sensor, a microcontroller, and a power source configured to power the electronic components;
a compartment space provided in the main body for storing a charging member in communication with at least one electronic component; and
at least one electronic indicator disposed on the main body and in communication with at least one of the one or more electronic components,
wherein the microcontroller is in communication with the at least one sensor and controls the at least one electronic indicator to display a value derived from data gathered by the sensor.

15. The electronic smoking device of claim 14, wherein the flow dispersing member includes an arched body and configured to provide at least two inhalation outlets.

16. The electronic smoking device of claim 14, wherein the electronic indicator comprises one or more light emitting diodes (LEDs), the LEDs configured to provide the value of inhalation material available for puffing stored in the inhalation material container or electrical charge available of the power source powering the electronic components.

17. The electronic smoking device of claim 14, wherein an LED is disposed within the internal space of the main body proximate to the proximal end of the main body, the LED configured to emit light of a wavelength effective for neutralizing bacteria and virus growth on the heating element and airborne within the inhalation material during inhalation use of the electronic smoking device.

18. The electronic smoking device of claim 14, wherein the internal space of the main body is configured to retain at least two inhalation material containers retaining inhalation material that are in fluid communication, and the electronic smoking device includes a valve mechanism in communication with one inhalation material container, and the valve mechanism is configured to control inhalation material flowing from the one inhalation material container and mixing with the other.

19. The electronic smoking device of claim 18, wherein the electronic indicator comprises a digital display, the digital display configured to provide a percentage amount of the one inhalation material flowing from the one inhalation material container and mixing with the other.

20. An electronic smoking device, comprising:
- a main body having a proximal end and a distal end, and including an internal space;
- a mouthpiece provided at the proximal end of the main body, the mouthpiece including an open terminal end having a flow dispersing member disposed thereon, the flow dispersing member projecting beyond at least two inhalation outlets at the open terminal end of the mouthpiece;
- at least one inhalation material container disposed within the internal space that includes an upper chamber, a lower chamber, and a conduit configured to pass inhalation material from the lower chamber toward the upper chamber;
- a plurality of electronic components that include a heating element, a plurality of sensors, a microcontroller, and a power source configured to power the electronic components;
- a compartment space provided in the main body for storing a charging member in communication with the power source; and
- at least one electronic indicator disposed on the main body and in communication with the microcontroller,
  - wherein the microcontroller is in communication with the plurality of sensors and controls the at least one electronic indicator to display a value derived from data gathered by the plurality of sensors, and
  - wherein the microcontroller is in electronic communication with the plurality of sensors and capable of regulating the heating element's heat output based on data from at least one sensor.

* * * * *